US00RE49008E

(19) United States
(12) Reissued Patent
Clausen et al.

(10) Patent Number: US RE49,008 E
(45) Date of Reissued Patent: Apr. 5, 2022

(54) METHOD OF COMPOSING AND DESIGNING A SET OF TEETH

(71) Applicant: 3Shape A/S, Copenhagen K (DK)

(72) Inventors: Tais Clausen, Klagshamn (SE); Rune Fisker, Virum (DK); Sven Nonboe, Hillerød (DK)

(73) Assignee: 3Shape A/S, Copenhagen K (DK)

(21) Appl. No.: 15/496,666

(22) Filed: Apr. 25, 2017

Related U.S. Patent Documents

Reissue of:
(64) Patent No.: 9,358,083
Issued: Jun. 7, 2016
Appl. No.: 13/579,462
PCT Filed: Feb. 17, 2011
PCT No.: PCT/DK2011/050048
§ 371 (c)(1),
(2) Date: Nov. 8, 2012
PCT Pub. No.: WO2011/100976
PCT Pub. Date: Aug. 25, 2011

U.S. Applications:
(60) Provisional application No. 61/306,150, filed on Feb. 19, 2010.

(30) Foreign Application Priority Data

Feb. 19, 2010 (DK) ..... PA 2010 00142

(51) Int. Cl.
*A61C 13/00* (2006.01)
*A61C 13/08* (2006.01)
*A61C 13/36* (2006.01)

(52) U.S. Cl.
CPC ..... *A61C 13/0004* (2013.01); *A61C 13/08* (2013.01); *A61C 13/082* (2013.01)

(58) Field of Classification Search
CPC ..... A61C 13/0004; A61C 5/77
(Continued)

(56) References Cited

U.S. PATENT DOCUMENTS 5,605,459 A 2/1997 Kuroda et al.
7,474,932 B2 * 1/2009 Geng ..... A61C 13/0004 433/167
(Continued)

FOREIGN PATENT DOCUMENTS

AU 2007296845 3/2008
CA 2725818 1/2010
(Continued)

OTHER PUBLICATIONS

3Shape A/S, 3Shape Dental Designer 2005—2 User Manual, published in Copenhagen, Denmark, pp. 1-37. (Year: 2005).*
(Continued)

*Primary Examiner* — Beverly M Flanagan
(74) *Attorney, Agent, or Firm* — Buchanan Ingersoll & Rooney PC

(57) ABSTRACT

Disclosed is a computer-implemented method of designing a number of dental restorations for a patient, wherein the method includes: selecting a composed set of teeth including a number of teeth, where the number of teeth are arranged spatially relative to each other forming a high aesthetic composition; applying the composed set of teeth to a virtual three dimensional representation of the patient's present oral situation to obtain an initial set of teeth; optionally modifying one or more parameters of one or more of the teeth in the initial set of teeth to obtain a finalized set of teeth.

27 Claims, 6 Drawing Sheets

(58) Field of Classification Search
USPC ..... 433/201.1, 213, 214
See application file for complete search history.

(56) References Cited

U.S. PATENT DOCUMENTS

| | | | | |
|---|---|---|---|---|
| 7,950,131 | B2 * | 5/2011 | Hilliard | A61C 13/0027 433/6 |
| 8,425,229 | B2 * | 4/2013 | Nilsson et al. | A61C 13/0004 433/172 |
| 8,706,672 | B2 * | 4/2014 | Malfliet | G06T 7/0012 706/47 |
| 8,727,776 | B2 * | 5/2014 | Mehl | 433/223 |
| 2004/0220691 | A1 | 11/2004 | Hofmeister et al. | |
| 2006/0063135 | A1 | 3/2006 | Mehl | |
| 2007/0003907 | A1 | 1/2007 | Chishti et al. | |
| 2009/0034811 | A1 | 2/2009 | Kuo | |
| 2010/0021859 | A1 * | 1/2010 | Kopelman | A61C 8/0001 433/50 |
| 2010/0049351 | A1 | 2/2010 | Monkmeyer | |

FOREIGN PATENT DOCUMENTS

| | | | |
|---|---|---|---|
| CN | 1678254 | | 10/2005 |
| CN | 1764421 | | 4/2006 |
| CN | 101548911 | | 10/2009 |
| EP | 2 322 115 | A1 | 5/2011 |
| JP | 2002272763 | | 9/2002 |
| JP | 2003-135488 | A | 5/2003 |
| JP | 2010-17467 | A | 1/2010 |
| JP | 2010-017467 | A | 1/2010 |
| WO | 2004/044787 | A2 | 5/2004 |
| WO | 2008/128700 | A1 | 10/2008 |
| WO | 2008/145293 | A2 | 12/2008 |

OTHER PUBLICATIONS

International Search Report (PCT/ISA/210) dated May 4, 2011, by the Danish Patent Office as the International Search Authority in corresponding International Application No. PCT/DK2011/050048. (2 pages).

Office Action (Notice of Reasons for Rejection) dated Jul. 22, 2014, by the Japanese Patent Office in corresponding Japanese Patent Application No. 2012-553181 and an English Translation of the Office Action. (10 pages).

The extended European search report dated Feb. 22, 2019, by the European Patent Office in corresponding European Patent Application No. 18209790.7. (6 pages).

Extended European Search Report issued in corresponding European Patent Application No. 20191305.0-1126, dated Nov. 9, 2020 (7 pages).

Sun, Yuchun, et al. "Study on CAD & RP for Removable Complete Denture" Computer Methods & Programs in Biomedicine, vol. 93, issue 3, pp. 266-272 (Nov. 2008) available from <http://www.sciencedirect.com/science/article/pii/S0169260708002496#>.*

An English language translation of the Office Action (Notice of Reason for Rejection) issued on Jul. 22, 2014, in corresponding Japanese Patent Application No. 2012-553181. (6 pages).

* cited by examiner

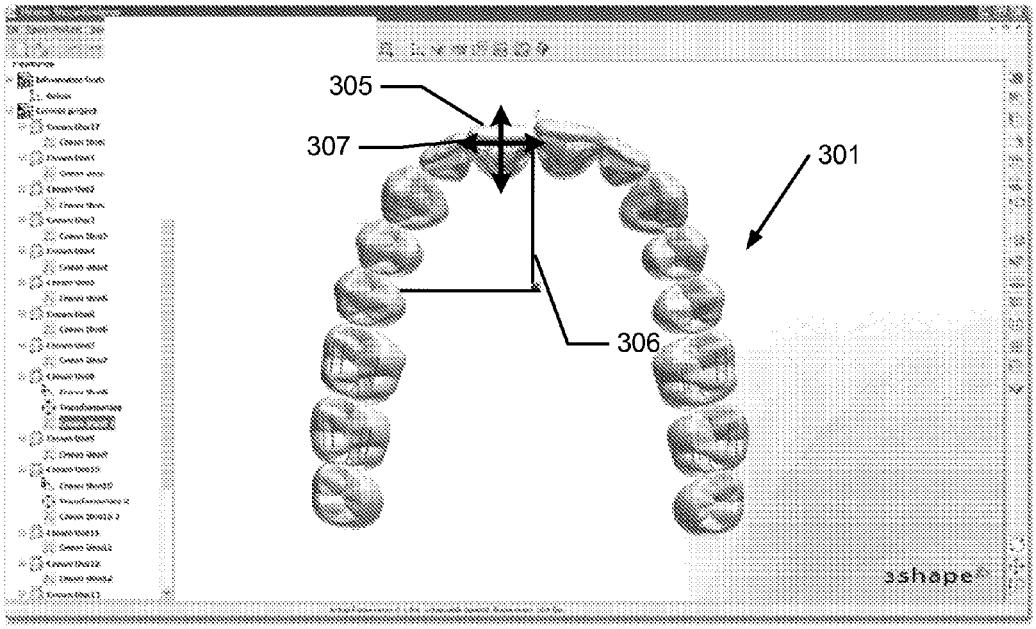
*Fig. 3*
*Fig. 4*
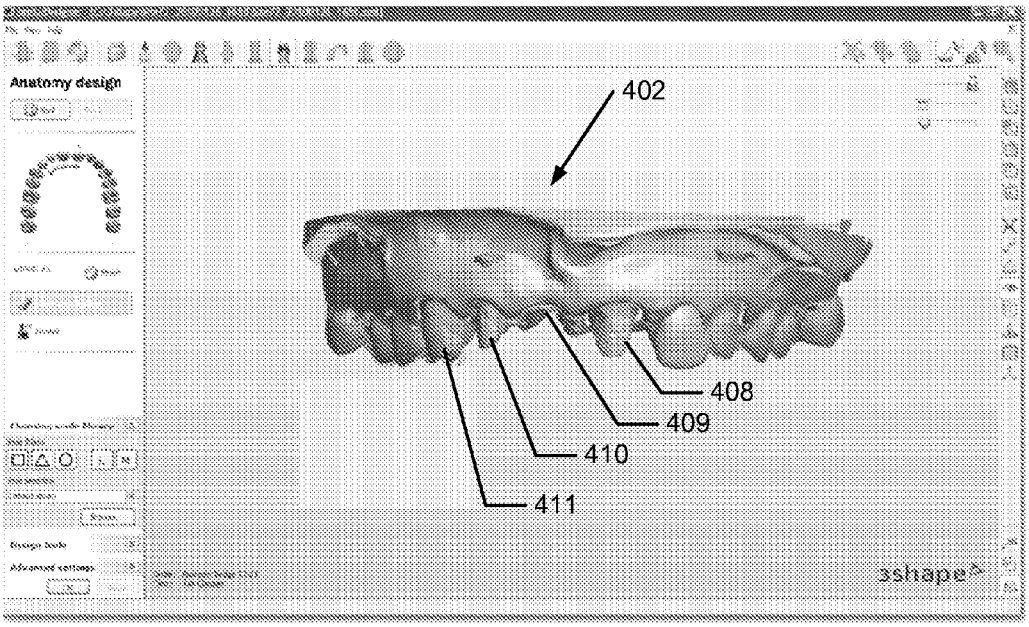

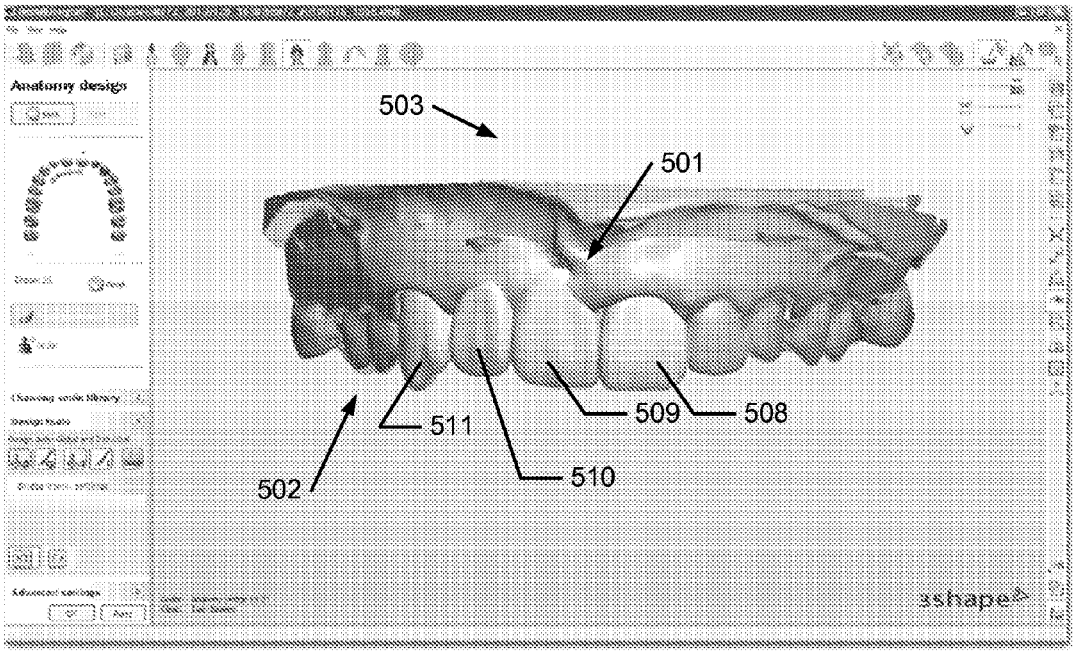
*Fig. 5*
*Fig. 6a*
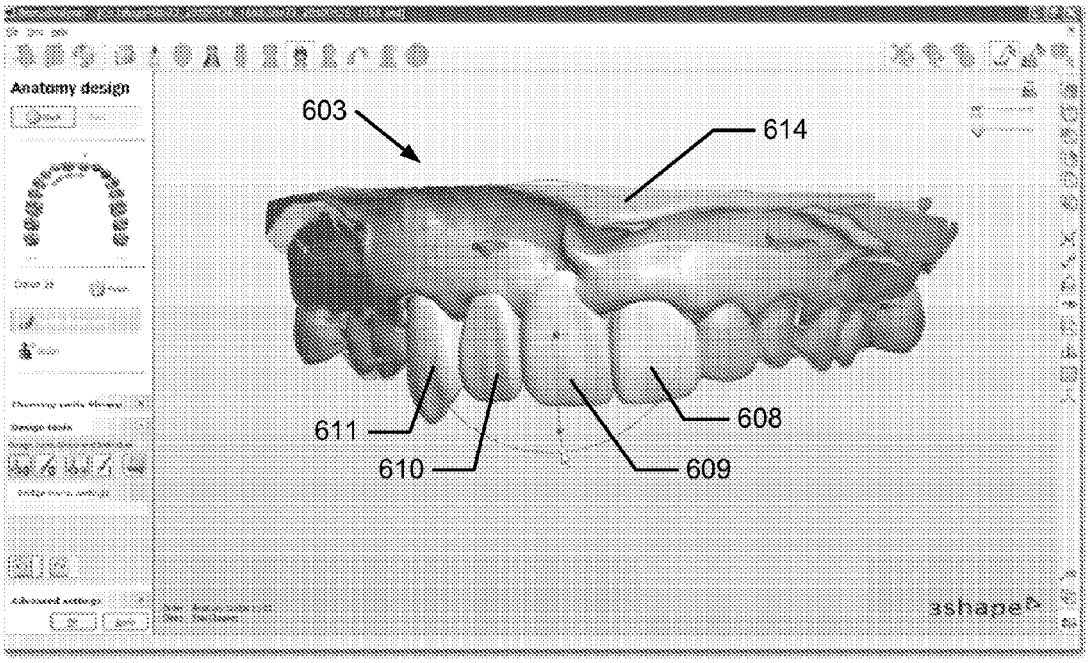

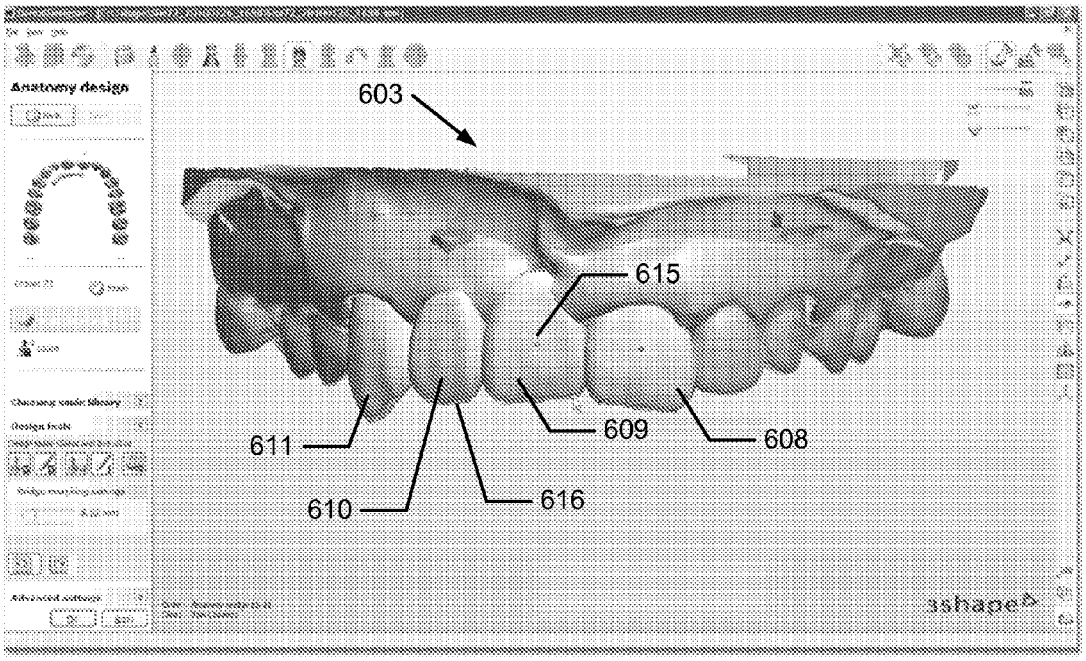
*Fig. 6b*
*Fig. 7a*
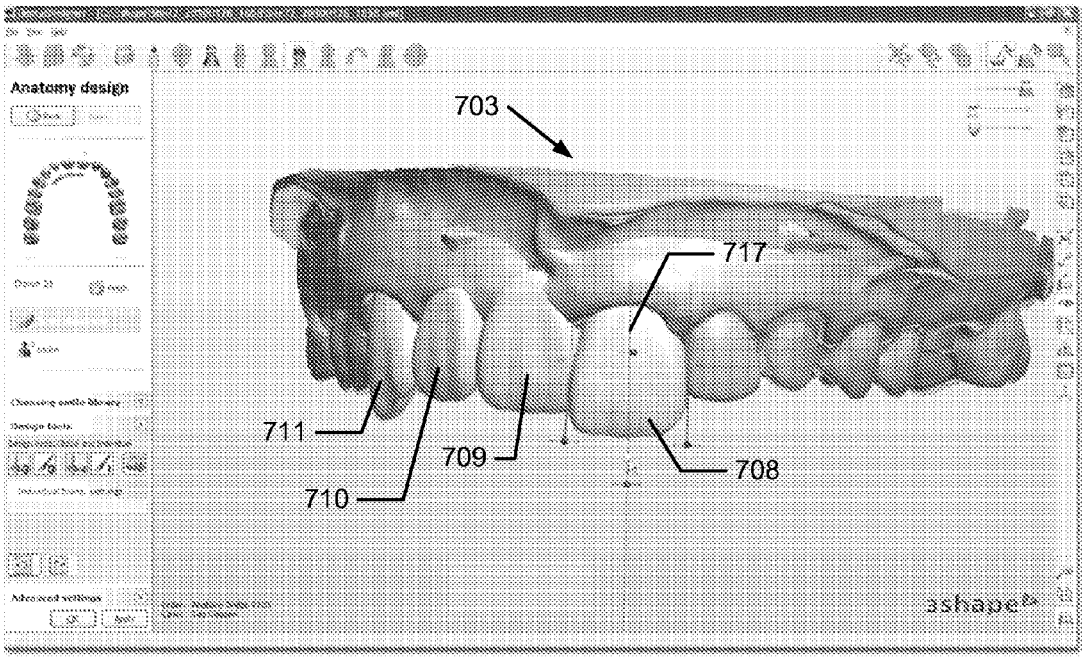

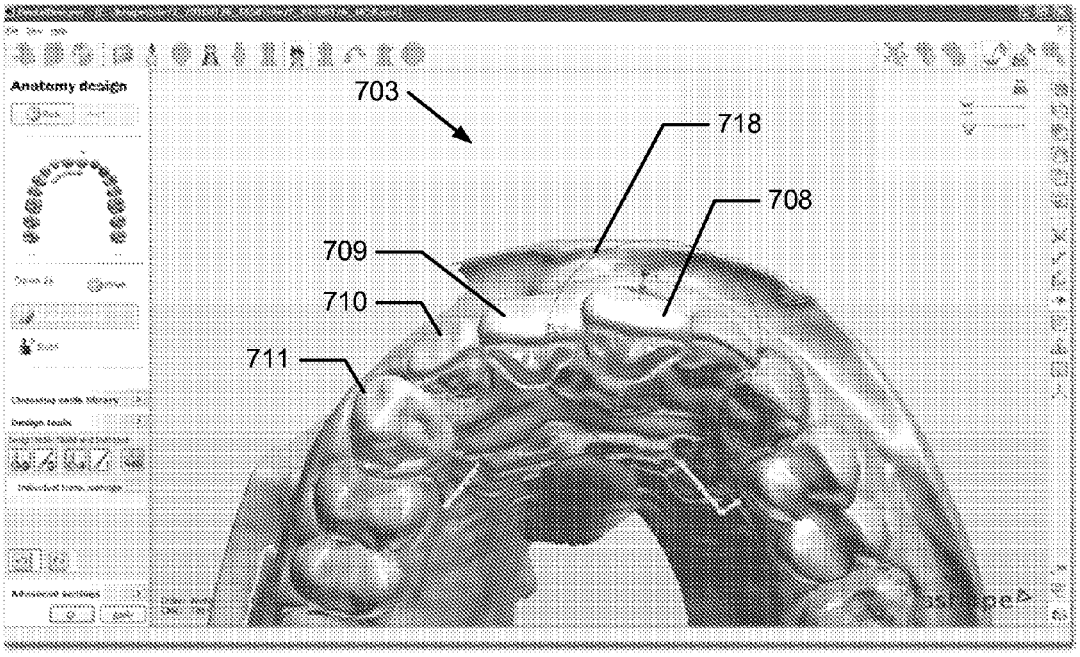
*Fig. 7b*
*Fig. 8*
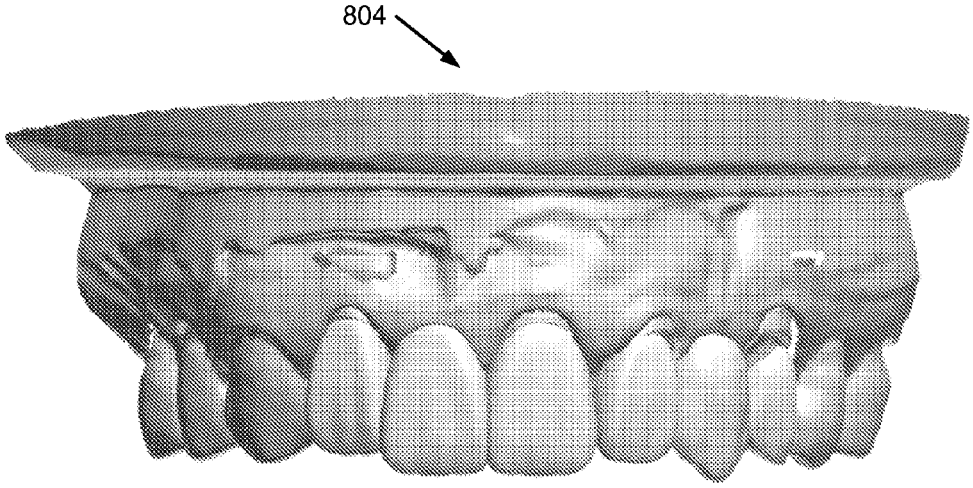

*Fig. 9a*
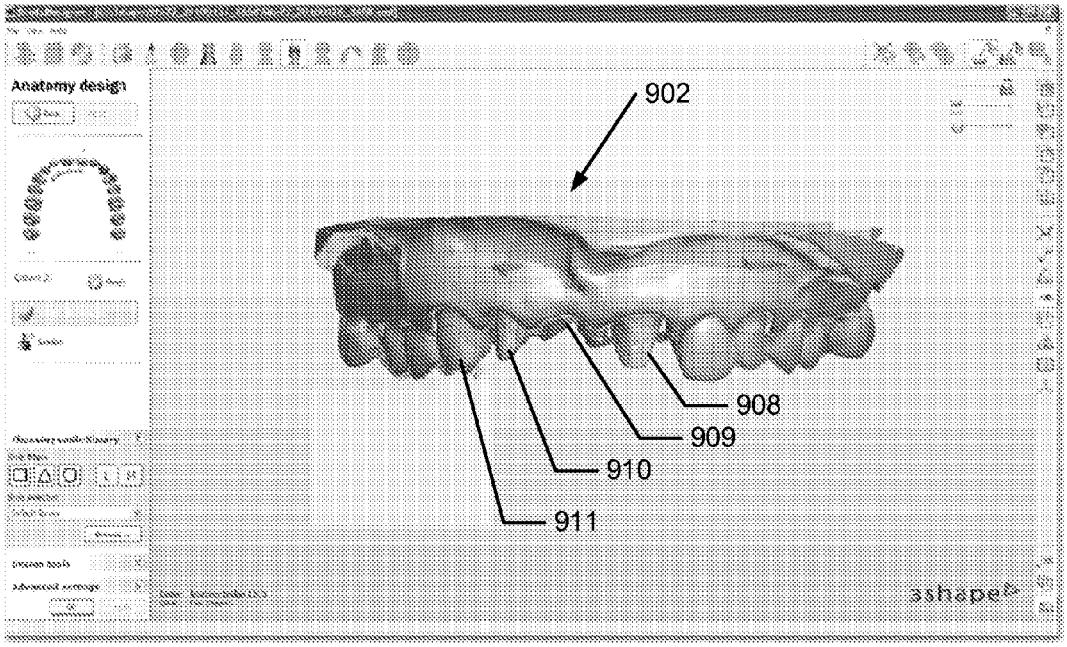
*Fig. 9b*
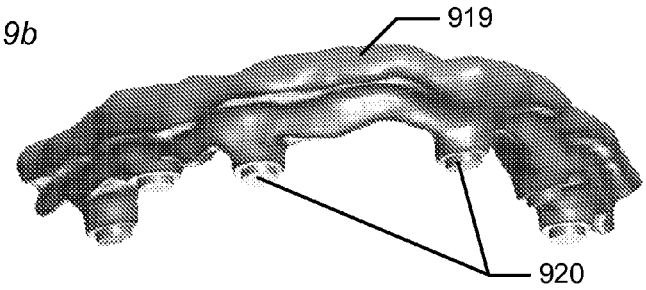
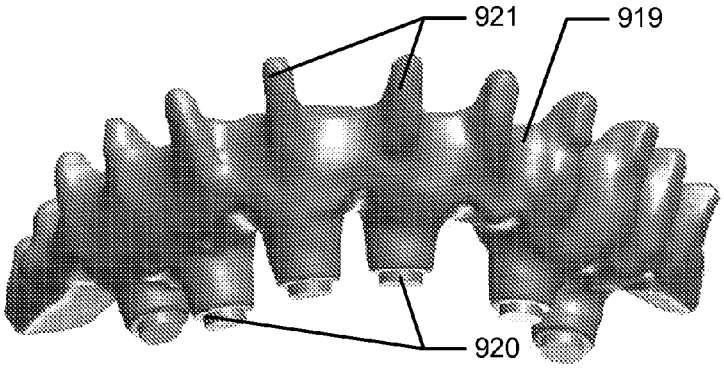
*Fig. 9c*

METHOD OF COMPOSING AND DESIGNING A SET OF TEETH

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

This invention generally relates to a computer-implemented method of designing a number of teeth for a patient.

BACKGROUND OF THE INVENTION

When a patient requires a dental restoration, such as crowns, bridges, abutments, or implants, the dentist will prepare the teeth e.g. a damaged tooth is grinded down to make a preparation where a crown is glued onto. An alternative treatment is to insert implants, such as titanium screws, into the jaw of the patient and mount crowns or bridges on the implants. After preparing the teeth or inserting an implant the dentist can makes an impression of the upper jaw, the lower jaw and a bite registration or a single impression in a doublesided tray (also known as triple trays).

The impressions are sent to the dental technicians who manufacture the restorations e.g. the bridge. The first step to manufacture the restoration is traditionally to cast the upper and lower dental models from impressions of the upper and the lower jaw, respectively. The models are usually made of gypsum and often aligned in a dental articulator using the bite registration. The articulator simulates the real bite and chewing motion. The dental technician builds up the dental restoration inside the articulator to ensure a nice visual appearance and bite functionality. A proper alignment of the cast in the articulator is crucial for the final restoration.

CAD technology for manufacturing dental restoration is rapidly expanding improving quality, reducing cost and facilitating the possibility to manufacture in attractive materials otherwise not available. The first step in the CAD manufacturing process is to create a 3-dimensional model of the patient's teeth. This is traditionally done by 3D scanning one or both of the dental gypsum models. The 3-dimensional replicas of the teeth are imported into a CAD program, where the entire dental restoration, such as a bridge substructure, is designed. The final restoration 3D design is then manufactured e.g. using a milling machine, 3D printer, rapid prototyping manufacturing or other manufacturing equipment. Accuracy requirements for the dental restorations are very high otherwise the dental restoration will not be visual appealing, fit onto the teeth, could cause pain or cause infections.

SUMMARY

Disclosed is a computer-implemented method of designing a number of dental restorations for a patient, wherein the method comprises:

selecting a composed set of teeth comprising a number of teeth, where the number of teeth are arranged spatially relative to each other forming a high aesthetic composition;

applying the composed set of teeth to a virtual three dimensional representation of the patient's present oral situation to obtain an initial set of teeth;

optionally modifying one or more parameters of one or more of the teeth in the initial set of teeth to obtain a finalized set of teeth.

The dental restoration(s) may be the physical realisation of the designed finalized set of teeth. Thus in order for physically providing the finalized set of teeth to the patient, a number of dental restorations may be performed.

Consequently, it is an advantage that the method provides that larger dental restorations, such as partial or full dentures, can also easily and effectively be made using CAD technology.

Conventionally, primarily smaller dental restorations such as crowns and bridges on a couple of teeth are made using CAD technology. But by means of the present method, larger dental restorations can advantageously be made, because the designed dental restorations or teeth are made from an interrelated composed set of teeth, whereby it is easy and fast to design the new teeth, because the starting point is a set of teeth where the teeth are arranged spatially relative to each other forming a high aesthetic composition. Traditionally, the user would have to arrange every single tooth separately, which is very time consuming if several teeth should be designed. Thus traditionally, the teeth are stored separately in a CAD program, which is fine when making smaller dental restorations such as crowns and bridges, where only one or a few designed teeth are used. But according to the present method, the designed teeth are stored or can be composed as a whole set of interrelated teeth facilitating that larger dental restorations comprising a high number of teeth can be designed. A high aesthetic composition is defined as providing an aesthetically pleasing, visually pleasing, nice, beautifully looking, e.g. symmetrical, smile.

It is an advantage that a user can create a set of teeth for a patient, where the starting point in the process is a composed set of teeth comprising a number of teeth. Thus the composed set of teeth is a number of teeth, i.e. more than one teeth, for example two teeth, four teeth, seven teeth or all teeth in the upper and/or lower arch of the mouth. The teeth in the composed set of teeth are arranged spatially relative to each other and interrelated with each other. The spatial arrangement or interrelation may comprise the position, direction, rotation, height etc. of the teeth relative to each other. Thus the composed set of teeth is an entirety of interrelated teeth, instead of a number of single, individual teeth which can be arranged side by side as known from prior art.

Thus it is an advantage of the invention that the user can create nice dental restorations or a nice set of teeth for the patient by using a composed set of teeth as a starting point. The composed set of teeth provides better quality and e.g. symmetry of the designed teeth.

It is an advantage that the composed set of teeth are interrelated, because this makes it very easy for the user to very quickly design a desired set of teeth. According to prior art computer-implemented methods of designing teeth, the separate teeth for making a dental work on more than one tooth is selected one by one, i.e. when making a bridge covering three teeth, three separate teeth was selected and arranged side by side on a line where the bridge should be. This in prior art the teeth must be modified individually, one at a time, and, it is highly probable that the modifications the user is making to one tooth will not match the modification of another tooth or of all the other teeth, so one little modification on one tooth can destroy the entire aesthetics, and the user must repeatedly perform new modifications to restore the aesthetics of all teeth. But when the starting point for designing a number of teeth is a number of composed, interrelated teeth, and not single teeth, it is much easier and faster for the user to design a nice set of teeth in a short time.

The patient may have several different reasons for having a dental restoration made, for example cosmetic reasons if the patient wishes to have nicer teeth, for health reasons if the patient has bad or poor teeth, if the patient has been in an accident where some or all of his/hers teeth were broken etc.

Thus it is an advantage that the set of teeth can be designed to look very much or exactly like the patient's original non-broken set of teeth by selecting a composed set of teeth which resembles the patient's original set as good as possible and then modifying one or more parameters for the teeth corresponding to the patient's original set of teeth so that the finalized set of teeth completely or nearly completely resembles the special look of the patient's original set of teeth.

The user can be a dental technician, a dentist etc.

It is an advantage that all the patient's teeth can be replaced with the teeth designed according to the method or just some of the patient's teeth can be replaced. The expression "set of teeth" means a number of teeth, e.g. six teeth or e.g. the complete set of teeth a patient can have.

The patient's oral situation can belong to one or more of the following cases:

no teeth left;

one or more teeth left;

one or more preparations;

one or more implants;

The present method is a method of designing a number of dental restorations, thus the method relates to the field of restorative dentistry or prosthodontics, also known as dental prosthetics or prosthetic dentistry, which is associated with missing or deficient teeth. Thus restorative and prosthetic dentistry are different technical fields than orthodontics. Orthodontics is concerned with displacement of teeth due to malocclusion, where the teeth are moved into desired positions by means of wires and brackets or braces or shells, which the patient must wear over longer time periods. Thus in orthodontics the teeth are displaced, whereas in restorative dentistry the teeth are restored, e.g. crowns, bridges, abutments, implants, dentures etc. are made and arranged in the patient's mouth. So in orthodontics the teeth are moved relative to each other, whereas in restorative dentistry one or more teeth are at least partly replaced with a restoration in the form of a crown, implant, denture etc. Or where a tooth is missing, a restoration is made, such that the missing tooth is replaced with a restoration, e.g. a pontic in a bridge, an implant etc. Thus a dental restoration refers to the replacement of missing tooth structure.

Dental restorations may comprises crowns, bridges, pontics, abutments, implants, dentures, inlays, onlays, post and core or inlay core, removables etc.

In some embodiments the method further comprises optionally modifying the entire initial set of teeth collectively, when optionally modifying the one or more parameters in the initial set of teeth.

It is an advantage that the user very quickly can modify one or more parameters for the entire initial set of teeth, since hereby the initial set of teeth can be designed quickly and reliable. It is an advantage that the user can visually see and therefore test and evaluate different modifications for the initial set of teeth to evaluate which set of teeth is the best for the specific patient. Thus collective modification of the entire initial set of teeth allows for easy and quick testing of different teeth designs and looks, and this interactive modification of the initial set of teeth is both an advantage for the patient and the user, since both can actually see the different ways the teeth can look like.

Modifying the entire set of teeth collectively at one go may be denoted global modification or common modification or collective modification.

Modifying one tooth at a time may be denoted local modification or individual modification or separate modification or single modification.

Thus the method provides that the teeth can be modified both commonly and individually. This is an advantage because modifications which should apply for all teeth can be modified collectively in order to ensure a fast and identical modification, e.g. that all teeth should be 0.2 mm longer, whereas a modification which should just apply for a single tooth can be applied individually, e.g. if just one tooth should be a little crooked relative to the rest of the teeth.

It is an advantage that the method comprises the option of modifying the entire set of teeth collectively at a time or at one go, because this saves a lot of time for the user who is designing the set of teeth for the patient. Traditionally the user could only modify one tooth at a time, because software applications for teeth design or teeth restorations only supported the modification of one tooth at a time. Conventionally, designing entire teeth sets for a patient has previously been performed by manual handcraft, because modifying one tooth at a time digitally is also time consuming. It is therefore an advantage that several teeth or an entire set of teeth can be modified collectively, since it provides a better result and saves a lot of time.

It is an advantage that the teeth can be modified collectively due to their interrelation according to this method, because it makes it very easy for the user to very quickly design a nice set of teeth. According to prior art methods, only one tooth could be modified at a time, and if each tooth is modified separately, it is highly probable that the modifications the user is making to one tooth will not match the modification of another tooth or of all the other teeth, so one little modification on one tooth can destroy the entire aesthetics, and the user may repeatedly perform new modifications to compensate for the previous ones. But when the entire set of teeth can be modified as a whole according to the present method, it is much easier and faster for the user to design a nice set of teeth in a short time.

A coordinate system for the whole or entire set of teeth may be defined, a coordinate system for each individual tooth may be defined, and a coordinate system for the face may be defined.

The different coordinate systems may be shown on the screen depending on the mode the program is in.

Each individual tooth in a set of teeth can be saved or stored individually, and its interrelation to the other teeth is also saved.

It is a further advantage that if the patient originally had quite short teeth for instance, and the patient has broken his teeth and wishes to have a new set of teeth looking like the original set of teeth, and if there is no composed set of teeth available that resembles the patient's original short teeth, then the initial set of teeth can collectively at one go become shortened, such that the finalised set of teeth really resembles the specific wishes of the patient.

In some embodiments the method further comprises optionally modifying a number of teeth in the initial set of teeth collectively, when optionally modifying the one or more parameters in the initial set of teeth.

Thus besides modifying the entire set of teeth at one go or modifying a single tooth at a time, a number of teeth can be modified collectively, i.e. a subset, e.g. five of the teeth, in a larger set of teeth can be modified collectively. This may be denoted group modification or subset modification.

In some embodiments the method further comprises selecting at least a number of the designed dental restorations or teeth for manufacturing.

The finalized set of teeth is the virtual design of the new set of teeth. In order for providing the new teeth to the patient a number of dental restorations may be required. Thus in order for manufacturing these new teeth, the required dental restorations may be determined. The dental restorations may be based on the difference between the existing teeth and the designed teeth in the finalized set of teeth. If the patient e.g. misses an entire tooth or an entire tooth needs to be pulled out of the patient's mouth, then for example an implant with an abutment and/or crown or veneering may be manufactured and incorporated at the place of the missing tooth, or a bridge may be manufactured where a pontic is arranged at the place of the missing tooth. The bridge may be attached to the neighbor teeth, and thus the two neighbor teeth may be prepared by grinding them such that a crown can be attached on each neighbor teeth. Thus based on the finalized set of teeth, it may be determined that one or more dental restorations are required to obtain the finalized set of teeth, and these dental restorations may thus be designed. For example it may be determined that the finalized set of teeth requires that a bridge is made, e.g two crowns with a pontic in between should be made and these two teeth should be prepared for attachment of the crowns, and one normal crown not included in a bridge may also be required as well as an implant with a crown on the implant abutment.

In some embodiments the method further comprises optionally modifying one or more parameters of one or more of the teeth in the composed set of teeth before applying the representation of the patient's present oral situation to obtain a modified composed set of teeth.

It is an advantage that modifications can be made to the composed set of teeth, since hereby modifications which should for example definitely be made, can be made already up front in the design process. For example if the patient wishes that his central teeth should be crocked in a certain way, the user can make this modification to the central teeth in the composed set of teeth, such that the design with the crocked central teeth is the starting point for the potential further modifications. This may make the design process faster and more user-friendly, since the modifications can be performed in different steps. Thus modifications on the set of teeth can be made both before the patient's present oral situation or present set of teeth are applied to the composed set of teeth and after the patient's present oral situation or present set of teeth has been applied to the composed set of teeth. Thus the composed set of teeth may be a regular or template composed set of teeth or a modified composed set of teeth.

In some embodiments the method further comprises obtaining the three dimensional virtual representation of the patient's present oral situation by scanning the present oral situation using an intraoral scanner and/or scanning the surface of a negative impression of the patient's present oral situation and/or scanning the surface of a positive model of the patient's present oral situation.

It is an advantage to obtain a 3D representation of the patient's present oral situation or present set of teeth since the composed set of teeth can be overlayed on the present teeth to match and/or compared the two sets of teeth, and when the virtual representation of the oral situation is obtained by some means of scanning, the representation can be of very high quality such that the final design or finalized set of teeth will be of very high quality and with a good match to the remaining teeth.

In some embodiments the method further comprises obtaining a three dimensional virtual representation of the patient's original set of teeth by scanning the original set of teeth using an intraoral scanner and/or scanning the surface of a negative impression of the patient's original teeth and/or scanning the surface of a positive model of the patient's original teeth, where the representation of the original set of teeth is provided before the patient's teeth are prepared.

It is an advantage that before the set of teeth are prepared, a so called pre-preparation scan can be made, so that the patient's original set of teeth can be visualized too, so that the user can take account of the patient's original teeth when designing the new teeth in order to provide a finalized set of teeth which is a perfect replica or imitation of the patient's original set of teeth, if this is what the patient wishes.

In some embodiments the one or more parameters comprise:

the curve of the teeth defined by the relative position of teeth.

In some embodiments the one or more parameters comprise:

the scaling of the teeth.

The scaling of the teeth comprises the length, the width etc of the teeth.

In some embodiments the one or more parameters comprise:

the rotation of teeth relative to the median line of the face.

In some embodiments the rotation of teeth relative to the median line of the face creates a composition or a combination of compositions selected from:

a basic aesthetic composition;

a strong aesthetic composition; or a soft aesthetic composition.

It is an advantage that the rotation of the teeth relative to the median line of the face can be modified, because this angle is important for the aesthetic look of the teeth. There may be three typical or classical aesthetic compositions for the rotation of the teeth; the basic aesthetic composition, where the rotation of the teeth is neutral or normal relative to the median line; the strong aesthetic composition, where the rotation is such that the distal point of a tooth is turned outwards relative to the median line; and the soft aesthetic composition, where the distal point of the tooth is turned inwards relative to the median line.

Thus it is an advantage that the rotation of the teeth provides one of or a combination of the three classical compositions.

In some embodiments the one or more parameters comprise:

the geometric shape of the central teeth.

In some embodiments the geometric shape of the central teeth is or is a combination selected from:

an oval shape;

a triangular shape; or a rectangular/square shape.

It is an advantage that the geometric shape of the teeth can be modified, because the shape of the teeth is important for the aesthetic look of the teeth. There may be three different typical or classical types of shape of a central tooth; an oval shape, where the light reflected from the labial surface of the tooth resembles a round or an oval shape; a triangular shape, where the light reflected from the labial surface of the tooth resembles a triangular shape; and a rectangular/square shape, where the light reflected from the labial surface of the tooth resembles a rectangular/square shape.

In some embodiments the one or more parameters comprise:

the geometric shape of the premolars and/or molar.

For the premolar and molar teeth the geometric shape may be denoted e.g. N, T, K.

In some embodiments the one or more parameters comprise:

the length of the teeth.

It is an advantage that the length of the teeth can be modified, because the length of the teeth is important for the aesthetic look of the teeth. Teeth length can be measured in millimeters or other measuring systems.

In some embodiments the one or more parameters comprise:

the length of the teeth relative to other teeth.

It is an advantage that the relative length of the teeth can be modified, because the relative length of the teeth is important for the aesthetic look of the teeth.

In some embodiments the one or more parameters comprise:

the size of specific teeth relative to other specific teeth.

In some embodiments the one or more parameters comprise:

the size of lateral teeth relative to the central teeth.

It is an advantage that the size of e.g. the lateral teeth relative to the central teeth can be modified, because the relative size the teeth, or the size of teeth relative to other teeth, is important for the aesthetic look of the teeth.

For example the size of the lateral teeth may about 61.8% of the size of the central teeth, which corresponds to the golden proportion which the human brain experiences as visually pleasing or attractive. Another example is that the laterals may be 77% the size of the centrals, which however may appear to be too large for some patients. Yet another example is that the laterals may be ⅔ the size of the centrals. However, the size of the lateral teeth relative to the central teeth may be any other relation decided by the user and/or the patient.

In some embodiments the one or more parameters comprise:

the size of cuspid teeth relative to the lateral teeth.

It is an advantage that the size of, e.g., the cuspid or canine teeth relative to the lateral teeth can be modified, because the relative size of the teeth, or the size of teeth relative to other teeth, is important for the aesthetic look of the teeth.

For example the size of the cuspid or canine teeth may about 61.8% of the size of the lateral teeth, which corresponds to the golden proportion which the human brain experiences as visually pleasing or attractive. Another example is that the cuspids may be ⅔ the size of the laterals, which however may appear to be too large for some patients. However, the size of the cuspids teeth relative to the lateral teeth may be any other relation decided by the user and/or the patient.

In some embodiments the one or more parameters comprise:

the size of the gap between teeth.

It is an advantage that the size of the gap between teeth can be modified, because the size of the gap between teeth is important for the aesthetic look of the teeth. The gap between the central teeth in the upper and/or lower arch may be modified, and this gap is the most visual gap. However, all or some gaps may be modified.

In some embodiments the one or more parameters comprise:

shape of the teeth.

It is an advantage that the shape or morph of the teeth can be modified, because the general shape of the teeth is important for the aesthetic look of the teeth. Shaping or morphing may comprise smoothing, deforming, relocating, deleting or adding material. E.g. when relocating material, material from the thickest part of a tooth can be moved to a narrower part of the tooth.

In some embodiments the method further comprises mirroring of teeth.

It is an advantage that mirroring can be performed, because then the user does not need to work on or modify all teeth which should be designed, the user can just design teeth in e.g. the left side of an arch, and then mirror the designed teeth to the right side of the arch. One or more teeth can be mirrored.

It is an advantage that mirroring can be performed, if the patient needs to have one or more teeth in e.g. his/hers left side of an arch designed, then the patient's real, unbroken teeth in the right side of the arch can be resembled or scanned and copied to the left side of the arch by mirroring.

In some embodiments the method further comprises cloning of teeth.

Cloning may comprise copying of teeth or creating new teeth similar to other teeth. The cloning may be cloning from one or more existing teeth, cloning from one or more pre-prepared teeth, i.e. before they were prepared, cloning from one or more teeth in a wax up scan etc.

In some embodiments the method further comprises providing collision mapping relative to the antagonist.

It is an advantage that the collision mapping with the antagonist can be provided, because hereby it is easy and fast for the user to check if there is actually space enough for the designed teeth in the mouth of the patient.

In some embodiments the method further comprises virtually fitting the finalized set of teeth to a virtual retention means.

The virtual retention means corresponds to the real retention means. The retention means is/are adapted for retaining the dental restorations, i.e. the new teeth. The dental restorations may be denoted the new teeth, the physical realization of the finalized set of teeth, prosthesis or prosthetic parts.

Thus the retention means may be the preparation tooth or die for a crown or bridge, the retention means may be the jaw bone for an implant, the retention means may be the implant for an abutment, the retention means may be the abutment for a crown, the retention means may be the artificial gingival part of a denture.

Thus the dental restorations or one or more of the artificial teeth in the finalized set of teeth may be attached to a retention means, such as to one or more retention means. If the finalized set of teeth is a bridge, then the retention means may be two prepared teeth or dies. If the finalized set of teeth is a number of teeth for a full or partial denture, the retention means may be the gingival part of the denture.

Fitting may also be denoted connecting.

The set of teeth may be attached to the retention means.

Thus designing a number of dental restorations may comprise determining the attachment of the dental restorations to the retentions means for realizing the finalized set of teeth.

In some embodiments the method further comprises cutting the finalized set of teeth to the retention means.

Cutting may also be denoted virtual cutting or digital cutting.

It is an advantage that the set of teeth is not virtually fitted, aligned or fixed to the retention means before the designing of the set of teeth is completed, because it may be easier and visually better to design the teeth when they are not fitted to the retention means. Furthermore, it requires less processing power of the processing unit to modify and/or move the set of teeth in the coordinate system, when the set of teeth is not fitted or fixed in the correct position, e.g. the anatomical position. The correct position may be based on the position of the retention means, such as preparations, and/or based on the margin line from a real or virtual model of the patient's teeth.

The transition or interface between the retention means, such as an existing preparation tooth, and the finalized set of teeth may be determined by a joint spline, and thus the retention means and the finalized set of teeth each have a spline, and these two splines are fitted together or joined at the transition or interface.

The transition or interface between the retention means and the finalized set of teeth may be determined for determining the dental restorations, e.g. the shape, size, internal form, external form, thickness etc.

The internal surface of the set of teeth or the dental restorations should fit onto, be cut, or connect to the external surface of the retention means. The internal surface of the dental restorations may correspond to the shape of the external surface of the retention means. There may be a cement gap between the dental restorations and the retention means, and this cement gap may have the same thickness along the entire surface or the thickness may vary, e.g. due to drill compensation etc.

Thus the set of teeth may comprise dental restorations, which may comprise or be a crown, which may be glued to a prepared tooth, a bridge that may be glued to one or more prepared teeth, a crown that may be glued to an implant abutment where the implant is screwed into the jaw bone, the set of teeth for a denture that may be inserted in the gingival part of the denture which is arranged, either removably or fixed, in the patients mouth.

In some embodiments the method further comprises virtually cutting the finalized set of teeth to the gingival.

The virtual cutting may be performed automatically. After designing the new teeth, the new teeth should be cut to the gingival of the virtual model so that the dental restorations, e.g. artificial teeth, produced based on the designed finalized set of teeth will fit to the real gingival in the patient's mouth in cases where the dental restoration is close to or in contact with the gingival.

In case of a denture, the finalized set of teeth may virtually be cut to the gingival, whereby the artificial teeth in the denture are produced so that they fit to the artificial gingival of the denture. The part of the artificial teeth which will be visible in the denture may be designed to fit to the gingival. There may be a part of the artificial teeth which will be non-visible in the denture, because they are arranged inside the gingival part of the denture. The artificial gingival is typically made of an acrylic material.

A pontic in a bridge may be automatically cut or fitted to a preparation line or margin line in the gingival.

The preparation line or margin line may be for the pontic. A gap or space between the pontic and the gingival may be defined. There may be no gap between the pontic and the gingival and this may correspond to a gap of zero millimeters.

A crown may be automatically cut or fitted to a preparation line or margin line in the gingival.

A gap or space between the crown and the gingival may be defined, and the gap may be zero millimeters.

In some embodiments the method further comprises fitting the finalized set of teeth to its anatomical correct position in the gingival.

It is an advantage that the set of teeth is not fitted, aligned or fixed to the gingival before the designing of the set of teeth is completed, because it is easier and visually better to design the teeth when they are not fitted to the gingival. Furthermore, it requires less processing power of the processing unit to modify and/or move the set of teeth in the coordinate system, when the set of teeth is not fitted or fixed in the correct anatomical position. The correct anatomical position may be based on the position of the retention means, such as preparations, and on the margin line from a real or virtual model of the patient's teeth.

The transition between an existing preparation tooth and the new, designed tooth may be determined by a joint spline, and thus the preparation and the designed tooth each have a spline, and these two splines are fitted together or joined at the transition.

In some embodiments the set of teeth may be fitted/cut to the retention means and/or to the gingival before the set of teeth becomes the finalized set of teeth. This may increase the processing time as the interface between the set of teeth and the retention means and/or gingival should then be calculated each time any change is made to the set of teeth, but it may in some cases be preferred by the user that the set of teeth is visualized correctly relative to the gingival.

In some embodiments the method further comprises virtually designing the retention means.

If for example the retention means, e.g. a tooth, is not prepared for attachment of the dental restoration(s) before the virtual three dimensional representation of the patient's oral situation is obtained, then the retention means may be virtually designed. The retention means may be designed based on the finalized set of teeth and the dental restorations.

The retention means may also be virtually designed even though they were already prepared prior to the virtual three dimensional representation of the patient's oral situation was obtained, because the designed finalized set of teeth or dental restoration may require or gain from that the retention means were prepared differently.

In some embodiments the method further comprises adding virtual guiding lines to be overlaid on the teeth.

It is an advantage that by adding guiding lines it becomes easier for the user to control the modifications of e.g. the rotation or angles of the teeth relative to each other, or modifying e.g. the length of teeth, since the length of the teeth can be measured by means of the guiding lines.

In some embodiments the method comprises designing dental restorations or teeth in the lower and/or upper arch and fitting the lower and upper arch together.

In some embodiments the composed set of teeth comprises a composed set of anterior teeth and a composed set of molar teeth, where each of the composed sets of teeth is selected separately.

It is an advantage that different parts of the composed set of teeth can be selected separately, since this provides even further options for designing an obtaining a desired finalized set of teeth.

In some embodiments the composed set of teeth is selected from an electronic library comprising a number of different composed sets of teeth, where the composed sets of teeth can be standard sets of teeth and/or can be added to the electronic library by the user.

It is an advantage that the composed sets of teeth can comprise typical combinations of the parameters which determine the set of teeth. For example the composed sets of teeth can comprise a strong composition with rectangular teeth, soft composition with rectangular teeth, a soft composition with oval teeth etc.

In some embodiments the method further comprises that the user has the option of generating the composed set of teeth by defining the one or more parameters of the composed set of teeth.

It is an advantage that a composed set of teeth can be generated dynamically this way. The parameters may be selected from the same set of parameters used when modifying the composed set of teeth. The user defines a number of parameters for the composed set of teeth, which could be the curve or smile curve, i.e. the relative position of the teeth and the height of teeth, the aesthetic composition, i.e. the rotation of the teeth, for example the basic, strong or soft composition, the shape of the central or front teeth, e.g. oval, triangular or rectangular shape terms, and the shape of the premolars and molars, and a composed set of teeth will be generated based on that.

In some embodiments the method comprises designing a permanent or a temporary prosthesis.

In some embodiments the method comprises designing a partial denture prosthesis or a full denture prosthesis.

The denture can be a removable or fixed denture.

In some embodiments the method further comprises scanning the contours of the patient's face by means of a face scanner for designing the dental restorations or set of teeth taking the patient's face into consideration.

It is an advantage to design the set of teeth taking the patient's face into consideration, because then the teeth can be adjusted to match the face, e.g. oval teeth may suit an oval face form, long teeth may suit an oblong face form etc. or vice versa. When performing a face scan, the midline is found, which can be advantageous or useful to use, when designing the teeth.

Alternatively and/or additionally, X-ray scanning can be used for obtaining information about the patient's face or bone structure, and this information can be used for designing the dental restorations or new teeth.

In some embodiments the method is configured to be performed in an existing electronic program for digital dental restoration work.

The present invention relates to different aspects including the method described above and in the following, and corresponding methods, devices, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a computer program product comprising program code means for causing a data processing system to perform the method, when said program code means are executed on the data processing system.

Disclosed is also a computer program product comprising a computer-readable medium having stored there on the program code means.

In particular, disclosed herein is a system for designing a number of dental restorations for a patient, wherein the system comprises:

means for selecting a composed set of teeth comprising a number of teeth, where the number of teeth are arranged spatially relative to each other forming a high aesthetic composition;

means for applying the composed set of teeth to a virtual three dimensional representation of the patient's present oral situation to obtain an initial set of teeth;

means for optionally modifying one or more parameters of one or more of the teeth in the initial set of teeth to obtain a finalized set of teeth.

The system may be a system for computer-implemented design. The system may be a computer-implemented system.

Designing a number of dental restorations may be denoted designing a set of teeth, thus disclosed is a computer-implemented method of designing a set of teeth for a patient, wherein the method comprises:

selecting a composed set of teeth comprising a number of teeth, where the number of teeth are arranged spatially relative to each other forming a high aesthetic composition;

applying the composed set of teeth to a virtual three dimensional representation of the patient's present oral situation to obtain an initial set of teeth;

optionally modifying one or more parameters of one or more of the teeth in the initial set of teeth to obtain a finalized set of teeth.

Disclosed is also a dental restoration for a patient designed by means of the method.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 3 shows an example of modification of a composed set of teeth.

FIG. 4 shows an example of a patient's present oral situation.

FIG. 5 shows an example of an initial set of teeth, where the composed set of teeth is applied to the patient's present oral situation.

FIG. 6 shows examples of collective modifications of different parameters of the initial set of teeth.

FIG. 7 shows examples of individual modifications of different local parameters of the initial set of teeth.

FIG. 8 shows an example of a finalised set of teeth.

FIG. 9 shows examples of retention means for the designed set of teeth.

DETAILED DESCRIPTION

In the following description, reference is made to the accompanying figures, which show by way of illustration how the invention may be practiced.

The method is performed in a computer program suitable for performing the method. A screen connected to the computer may be provided on which the user can view the user interface of the program, and by means of e.g. a computer keyboard, a computer mouse, a touch screen, a space ball, a touchpad etc. the user can perform demands, such as selecting features and modifying features viewed on the screen. The program performs calculations or shows the changes on the screen view corresponding to the demands the user has made. The program, in which the method can be performed, can be a part of a larger program, it can be a separate program, the program can have means for communicating with other programs, other hardware, software or firmware etc.

Figure 1:
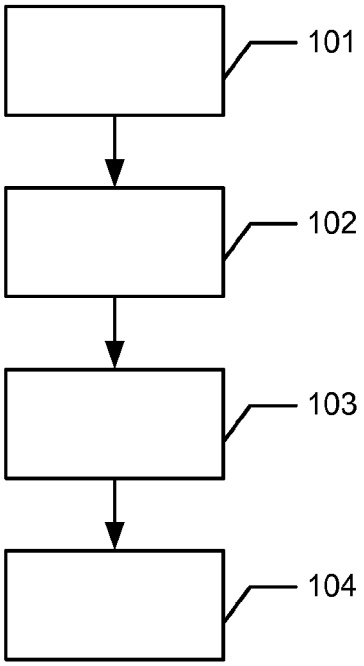
FIG. 1 shows an example of a flow chart of the method.

FIG. 1 shows an example of a flow chart of the method.

In step 101 a composed set of teeth is selected, where the composed set of teeth comprises a number of teeth, and where the number of teeth are arranged spatially relative to each other.

In step 102 a virtual three dimensional representation of the patient's present oral situation is provided.

In step 103 the composed set of teeth is applied to the virtual three dimensional representation of the patient's present oral situation to obtain an initial set of teeth.

In step 104 one or more parameters of one or more of the teeth in the initial set of teeth is modified to obtain a finalized set of teeth.

Figure 2:
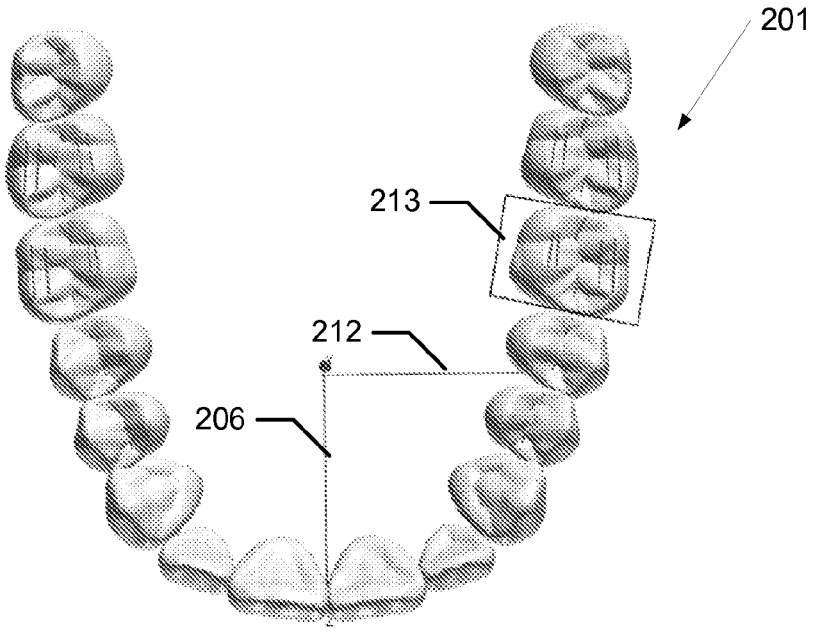
FIG. 2 shows an example of a composed set of teeth.

FIG. 2 shows an example of a composed set of teeth.

The composed set of teeth 201 is in this example seen from below and is the teeth of the upper arch. The figure shows an example of the curve of the teeth defined by the relative position of teeth. The composed set of teeth can be selected from an electronic library containing a number of different composed set or teeth, or the user can design the composed set of teeth himself by defining one or more parameters for the teeth. The teeth in the composed set of teeth 201 are arranged relative to each other, they are interrelated spatially.

The teeth in the composed set of teeth 201 can be selected based on a number of parameters, such as size, shape etc.

The median line 206 is shown and a line 212 perpendicular to the median line is shown. The function of the line 212 is for improved visual direction for the user. Thus a global coordinate system for the complete composed set of teeth is defined, whereby rotation, positioning etc. can be controlled for the complete composed set of teeth. The box 213 around the first molar tooth indicates that a coordinate system can be defined for each tooth, whereby rotation, positioning etc. can be controlled for each individual tooth.

FIG. 3 shows an example of modification of a composed set of teeth.

A tooth 305 in a composed set of teeth 301 is modified individually. In this example, the tooth 305 is rotated relative to the median line 306. A coordinate system 307 specific for the tooth 305 is shown on the tooth 305 for indicating to the user that that the program is in the mode, where the tooth can be modified with respect to positioning, e.g. rotation, translation etc. The tooth can also be modified for example with respect to shape, e.g. length, thickness, distribution of mass etc.

FIG. 3 and the following figures show screen-shots from a program where the method can be performed.

FIG. 4 shows an example of a patient's present oral situation.

The present oral situation 402 is in this example a case where the right central teeth 408, which may be denoted no. 9 in some dental notations, is prepared for a crown, the left central teeth no. 8, 409 is missing, the lateral teeth no. 7, 410, is also prepared for a crown, and the canine or cuspid no. 6, 411, is unmodified and not prepared for a dental restoration.

The present oral situation 402 can be a three dimensional virtual representation of the patient's present set of teeth or missing set of teeth. The three dimensional virtual representation can be obtained by scanning the patient's present oral situation or set of teeth using an intraoral scanner and/or scanning the surface of a negative impression of the patient's present teeth and/or scanning the surface of a positive model of the patient's present teeth.

FIG. 5 shows an example of an initial set of teeth, where the composed set of teeth is applied to the patient's present oral situation.

The initial set of teeth 503 is a combination of the composed set of teeth 501 and the patient's present oral situation 502. In this case, four teeth, 508, 509, 510, 511, from the composed set of teeth 501 are applied to the present oral situation 502. However, in other cases, all teeth from a composed set of teeth may be applied to the present oral situation, such that no present or original teeth are left. In other cases, more or less than four teeth from the composed set of teeth are applied to the present oral situation, depending on how many teeth the patient wishes to have exchanged.

FIG. 6 shows examples of collective modifications of different parameters of the initial set of teeth.

FIG. 6a shows an example of collective rotation of the initial set of teeth.

The parameter which is collectively modified is in this example rotation, and the modification is performed on the composed four teeth, 608, 609, 610, 611, in the initial set of teeth 603 with respect to the median line. The four composed teeth 608, 609, 610, 611 are all four rotated collectively so that they all have become skew with respect to the remaining teeth in present oral situation. The global or common rotation is indicated with a circle 614 with markers, and it is clearly seen that the composed teeth have been rotated simultaneously and uniformly or identically, for example if comparing the length of tooth 611 with the length of the corresponding teeth 511 in FIG. 5. This is an example of global rotation, where a number of teeth are rotated collectively, i.e. simultaneously and e.g. identically.

FIG. 6b) shows an example of collective shaping of the initial set of teeth.

The parameter which is collectively modified is in this example shaping or morphing, and the modification is performed on the composed four teeth 608, 609, 610, 611, in the initial set of teeth 603. The composed teeth 608, 609, 610, 611 are all four collectively reshaped or morphed such that their shape or geometry is changed simultaneously and uniformly or identically. The global or common shaping or morphing is indicated by dots 615 on the collectively modified teeth and by dots 616 forming a line along the biting edge of the collectively modified teeth. It is seen that the teeth 608, 609, 610, 611 have been collectively shaped or morphed with a point of origin at the mesial point of the biting edge of tooth 609, and that the shaping or morphing is directed to a small compression at the point of origin, whereby the two central teeth 609, 608 have got sloped biting edges, which are in opposite directions. The other composed teeth 610, 611 are only slightly reshaped or morphed as a result of the collective shaping or morphing with point of origin at tooth 609.

FIG. 7 shows examples of individual modifications of different local parameters of the initial set of teeth.

FIG. 7a) shows an example of individual scaling of a single tooth in the initial set of teeth.

The parameter which is individually modified is in this example scaling, and the composed tooth 708 in the initial set of teeth 703 is modified. The other composed teeth 709, 710, 711 are not modified in this example. The coordinate system 717 indicates the scaling of the tooth 708. By means of the scaling, tooth 708 can become bigger or smaller, longer or shorter, wider or narrower. In this case, the tooth 708 has been modified to be longer than before, i.e., tooth 708 is made longer than it was in the composed set of teeth.

When moving for example a pointer arrow by means of e.g. a computer mouse over a single tooth then the coordinate system 717 for that tooth is seen when the program is in the individual scaling mode.

FIG. 7b) shows an example of individual rotation of a single tooth in the initial set of teeth.

The parameter which is individually modified is in this example rotation, and it is the composed tooth 708 in the initial set of teeth 703 which is modified. The other composed teeth 709, 710, 711 are not modified in this example.

The initial set of teeth 703 is seen from below in this figure instead of from the front as in the other figures, since the individual rotation is better illustrated in this view. The rotation system 718 indicates the rotation of the tooth 708. The tooth 708 has been rotated with respect to the median line such that the mesial part of the tooth 708 points more outwards.

FIG. 8 shows an example of a finalised set of teeth.

The finalised set of teeth 804 is obtained when the modifications of the initial set of teeth are finished and no more modifications will be performed. The finalised set of teeth 804 is the set of the teeth that will be manufactured and inserted into the patient's mouth. The finalized set of teeth may be manufactured as a number of dental restorations.

FIG. 9 shows examples of retention means for the designed set of teeth.

FIG. 9a) shows an example where the retention means is a patient's present oral situation 902, which is in this example a case where the right central teeth 908, which may be denoted no. 9 in some dental notations, is prepared for a crown, the left central teeth no. 8, 909 is missing, the lateral teeth no. 7, 910, is also prepared for a crown, and the canine or cuspid no. 6, 911, is unmodified and not prepared for a dental restoration.

The present oral situation 902 can be a three dimensional virtual representation of the patient's present set of teeth or missing set of teeth. The three dimensional virtual representation can be obtained by scanning the patient's present oral situation or set of teeth using an intraoral scanner and/or scanning the surface of a negative impression of the patient's present teeth and/or scanning the surface of a positive model of the patient's present teeth.

FIG. 9b) shows an example where the retention means is an implant bridge 919 onto which a full denture is adapted to be arranged. On the side opposite to where the denture should be attached, the implant bridge 919 comprises protrusions 920 from holes for receiving implants (not shown). The implant bridge may be a standard bridge. Alternatively, the implant bridge may be customized for the patient and may be modeled automatically based on the shape of the patient's dental arch. The patient's dental arch may be determined by means of scanning the patient's mouth using an intraoral scanner and/or scanning the surface of a negative impression of the patient's mouth and/or scanning the surface of a positive model of the patient's mouth.

FIG. 9c) shows an example where the retention means is an implant bridge 919 comprising pins 921 where each pin is adapted to receive an artificial tooth having a hole in it for fitting over the pin, or where the pin is adapted to be covered by veneering in the form of e.g. ceramics or composite material for resembling teeth. On the side opposite to the pins 921, the implant bridge 919 comprises protrusions 920 from holes for receiving implants (not shown). The implant bridges shown in FIG. 9c) may be difficult to model automatically because the final shape of such an implant bridge is customized to the dental arch and the denture and as seen from the figures the implant bridges are not primarily based on standard geometrical forms. The implant bridge in FIG. 9c) may therefore be provided by cut-back of the preliminary model of the denture. From the figure it can be seen that the cut-back vary from tooth to tooth depending on the position of the tooth. The cut-back also varies depending on the type of the tooth and from which side of the tooth the cut-back is provided.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A system for designing [a number of] *one or more* dental restorations for a patient, wherein the system comprises*:*

*a display screen; and* a computer *connected to the display screen, wherein the computer is* configured to:

select a composed set of teeth comprising a number of teeth, where the number of teeth are arranged spatially relative to each other *and interrelated to each other* forming an arranged composition;

apply the composed set of teeth to a virtual three dimensional representation of the patient's present oral situation to obtain an initial set of teeth *including the composed set of teeth and present teeth of the patient*;

collectively modify*, in accordance with a coordinate system for the composed set of teeth,* the entire *composed set of teeth in the* initial set of teeth to obtain a finalized set of teeth, wherein the collective modification involves modifying the entire *composed* set of teeth simultaneously using the computer*, wherein the coordinate system for the composed set of teeth is defined specifically for the composed set of teeth*;

wherein the collective modification involves rotation of the *entire composed set of* teeth *with respect to the present teeth of the patient*.

2. The system according to claim 1, wherein the collective modification involves rotation of the teeth [relative to] *about* a median line of the patient's face.

3. A computer-implemented method of designing [a number of] *one or more* dental restorations for a patient, wherein the method comprises:

selecting a composed set of teeth comprising a number of teeth, where the number of teeth are arranged spatially relative to each other *and interrelated to each other* forming an arranged composition;

applying the composed set of teeth to a virtual three dimensional representation of the patient's present oral situation to obtain an initial set of teeth *including the composed set of teeth and present teeth of the patient*;

collectively modifying [a plurality of], *in accordance with a coordinate system for the composed set of teeth,* the *entire composed set of* teeth in the initial set of teeth to obtain a finalized set of teeth, wherein the collective modification involves modifying the [plurality] *entire composed set* of teeth simultaneously using the computer, *wherein the coordinate system for the composed set of teeth is defined specifically for the composed set of teeth*;

wherein the [method further comprises modifying the entire initial set of teeth collectively and the collective modification] *collectively modifying step* involves rotation of the *entire composed set of* teeth *with respect to the present teeth of the patient*.

4. The computer-implemented method according to claim 3, wherein the method further comprises:

modifying one or more parameters of the plurality of teeth in the composed set of teeth before applying the representation of the patient's present oral situation to obtain a modified composed set of teeth.

5. The computer-implemented method according to claim 3, wherein the collective modification involves rotation of teeth [relative to] *about* a median line of the patient's face.

6. The computer-implemented method according to claim 3, wherein the collective modification involves changing a geometric shape of the teeth in a center of the teeth.

7. The computer-implemented method according to claim 6, wherein the geometric shape of the central teeth is or is a combination selected from:

an oval shape;

a triangular shape; or a rectangular/square shape.

8. The computer-implemented method according to claim 3, wherein the method further comprises mirroring of teeth.

9. The computer-implemented method according to claim 3, wherein the method further comprises cloning of teeth.

10. The computer-implemented method according to claim 3, wherein the method further comprises providing collision mapping relative to an antagonist.

11. The computer-implemented method according to claim 3, wherein the method further comprises virtually fitting the finalized set of teeth to a virtual retainer.

12. The computer-implemented method according to claim 11, wherein the method further comprises cutting the finalized set of teeth to the retainer.

13. The computer-implemented method according to claim 11, wherein the initial set of teeth may be fitted/cut to the retainer and/or to the gingival before the set of teeth becomes the finalized set of teeth.

14. The computer-implemented method according to claim 11, wherein the method further comprises virtually designing the retainer.

15. The computer-implemented method according to claim 3, wherein the method further comprises virtually cutting the finalized set of teeth to the gingival.

16. The computer-implemented method according to claim 3, wherein the method further comprises fitting the finalized set of teeth to its anatomical correct position in the gingival.

17. The computer-implemented method according to claim 3, wherein the method further comprises adding virtual guiding lines to be overlaid on the initial set of teeth.

18. The computer-implemented method according to claim 3, wherein the selecting a composed set of teeth comprising a number of teeth involves selecting the composed set of teeth from an electronic library comprising a number of different composed sets of teeth.

19. The computer-implemented method according to claim 3, wherein the collective modification involves modifying the entire set of teeth uniformly using the computer.

20. The computer-implemented method according to claim 3, wherein the collective modification involves modifying the entire set of teeth identically using the computer.

21. A nontransitory computer readable medium storing thereon a computer program, where said computer program is configured for causing computer-assisted designing of a number of dental restorations by performing the method of claim 3.

*22. The system according to claim 1, wherein selecting the composed set of teeth includes selecting a set of teeth from a library and further selecting the number of teeth from the set of teeth selected from the library.*

*23. The system according to claim 1, wherein selecting the composed set of teeth includes selecting a set of teeth from a library and further selecting all of the teeth from the set of teeth selected from the library.*

*24. The system according to claim 23, wherein the composed set of teeth includes all of the teeth for a corresponding jaw.*

*25. A system for designing one or more dental restorations for a patient, wherein the system comprises:*

*a display screen; and*

*a computer connected to the display screen, wherein the computer is configured to:*

*select a composed set of teeth comprising a number of teeth, where the number of teeth are arranged spatially relative to each other and interrelated to each other forming an arranged composition;*

*apply the composed set of teeth to a virtual three dimensional representation of the patient's present oral situation to obtain an initial set of teeth including the composed set of teeth and present teeth of the patient;*

*collectively modify, in accordance with a coordinate system for the composed set of teeth, a plurality of teeth of the composed set of teeth in the initial set of teeth to obtain a finalized set of teeth, wherein the collective modification involves modifying the plurality of teeth simultaneously using the computer, wherein the coordinate system for the composed set of teeth is defined specifically for the composed set of teeth;*

*wherein the collective modification involves rotation of the plurality of teeth with respect to the present teeth of the patient.*

*26. A system for designing one or more dental restorations for a patient, wherein the system comprises:*

*a display screen; and*

*a computer connected to the display screen, wherein the computer is configured to:*

*select a composed set of teeth comprising a number of teeth, where the number of teeth are arranged spatially relative to each other and interrelated t each other forming an arranged composition;*

*apply the composed set of teeth to a virtual three dimensional representation of the patient's present oral situation to obtain an initial set of teeth including the composed set of teeth and present teeth of the patient;*

*collectively modify, in accordance with a coordinate system for the composed set of teeth, the entire composed set of teeth in the initial set of teeth to obtain a finalized set of teeth, wherein the collective modification involves modifying the entire composed set of teeth simultaneously using the computer, wherein the coordinate system for the composed set of teeth is defined specifically for the composed set of teeth;*

*wherein the collective modification involves rotation of the entire composed set of teeth with respect to gingiva of the patient.*

*27. A system for designing one or more dental restorations for a patient, wherein the system comprises:*

*a display screen; and*

*a computer connected to the display screen, wherein the computer is configured to:*

*select a composed set of teeth comprising a number of teeth, where the number of teeth are arranged spatially relative to each other and interrelated to each other forming an arranged composition;*

*apply the composed set of teeth to a virtual three dimensional representation of the patient's present oral situation to obtain an initial set of teeth including the composed set of teeth and present teeth of the patient;*

*collectively modify, in accordance with a coordinate system for the composed set of teeth, the entire composed set of teeth in the initial set of teeth to obtain a finalized set of teeth, wherein the collective modification involves modifying the entire composed set of teeth simultaneously using the computer, wherein the coordinate system for the composed set of teeth is defined specifically for the composed set of teeth;*

*wherein the collective modification involves rotation of the entire composed set of teeth with respect to gingiva of the patient and the present teeth of the patient.*

* * * * *